US010569032B2

(12) United States Patent
Suzuki et al.

(10) Patent No.: US 10,569,032 B2
(45) Date of Patent: Feb. 25, 2020

(54) NON-COMBUSTION TYPE FLAVOR INHALER

(71) Applicant: JAPAN TOBACCO INC., Tokyo (JP)

(72) Inventors: Akihiko Suzuki, Tokyo (JP); Manabu Takeuchi, Tokyo (JP); Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 126 days.

(21) Appl. No.: 15/824,547

(22) Filed: Nov. 28, 2017

(65) Prior Publication Data

US 2018/0078718 A1 Mar. 22, 2018

Related U.S. Application Data

(63) Continuation of application No. PCT/JP2015/065659, filed on May 29, 2015.

(51) Int. Cl.
*A61M 11/04* (2006.01)
*A24F 47/00* (2006.01)
(Continued)

(52) U.S. Cl.
CPC .......... *A61M 11/042* (2014.02); *A24F 47/00* (2013.01); *A24F 47/008* (2013.01); *A61M 11/001* (2014.02); *A61M 15/06* (2013.01)

(58) Field of Classification Search
CPC ... A47F 24/008; B05B 7/0018; B05B 7/1686; B05B 7/168; B05B 7/2459;
(Continued)

(56) References Cited

U.S. PATENT DOCUMENTS 4,268,460 A * 5/1981 Boiarski ............... A61M 11/06
128/200.16
5,144,962 A * 9/1992 Counts .................. A24F 47/008
131/194
(Continued)

FOREIGN PATENT DOCUMENTS

JP 2005-537919 A 12/2005
JP 2011-518567 A 6/2011
(Continued)

OTHER PUBLICATIONS

Extended European Search Report dated Dec. 7, 2018 for Application No. 15894111.2.
(Continued)

*Primary Examiner* — Cody J Lieuwen
(74) *Attorney, Agent, or Firm* — Birch, Stewart, Kolasch & Birch, LLP

(57) ABSTRACT

A non-combustion type flavor inhaler comprises: a reservoir storing an aerosol source; a transfer unit transferring the aerosol source from upstream of the liquid surface forming location to a liquid surface forming location at which a liquid surface of the aerosol source is formed, the transfer unit being configured to form the liquid surface; a suction port arranged downstream of the liquid surface forming location; a first atomizer atomizing the aerosol source located upstream of the liquid surface forming location; and a second atomizer atomizing a droplet generated from the liquid surface formed at the liquid surface forming location, the droplet being located downstream of the liquid surface forming location.

7 Claims, 7 Drawing Sheets

(51) Int. Cl.
*A61M 11/00* (2006.01)
*A61M 15/06* (2006.01)
(58) Field of Classification Search
CPC . B05B 7/2483; A61M 15/0001; A61M 15/06; A61M 11/001; A61M 11/003; A61M 11/04; A61M 11/041; A61M 11/042; A24F 47/008; A24F 47/00; A24F 47/002
USPC .................................................. 131/194, 273
See application file for complete search history.

(56) References Cited

U.S. PATENT DOCUMENTS

| | | | | |
|---|---|---|---|---|
| 2002/0079309 | A1* | 6/2002 | Cox | A61M 11/041 |
| | | | | 219/486 |
| 2004/0079368 | A1* | 4/2004 | Gupta | A61M 11/041 |
| | | | | 128/203.12 |
| 2004/0129793 | A1* | 7/2004 | Nguyen | A61M 11/041 |
| | | | | 239/13 |
| 2009/0272379 | A1 | 11/2009 | Thorens et al. | |
| 2014/0109905 | A1 | 4/2014 | Yamada et al. | |
| 2014/0334802 | A1 | 11/2014 | Dubief | |
| 2015/0320116 | A1* | 11/2015 | Bleloch | A61M 15/06 |
| | | | | 219/628 |
| 2016/0309784 | A1* | 10/2016 | Silvestrini | A61M 15/0066 |
| 2017/0360093 | A1* | 12/2017 | Fernando | A24F 47/004 |

FOREIGN PATENT DOCUMENTS

| | | |
|---|---|---|
| JP | 2015-504653 A | 2/2015 |
| TW | 201334713 A | 9/2013 |
| WO | WO 2013/027249 A1 | 2/2013 |
| WO | WO 2013/083634 A1 | 6/2013 |

OTHER PUBLICATIONS

International Search Report, issued in PCT/JP2015/065659, PCT/ISA/210, dated Aug. 18, 2015.
Office Action issued in Taiwan Patent Application No. 105106098 dated Dec. 20, 2016.

* cited by examiner

NON-COMBUSTION TYPE FLAVOR INHALER

CROSS REFERENCE TO RELATED APPLICATIONS

This application is a Continuation of PCT International Application No. PCT/JP2015/065659 filed on May 29, 2015, which is hereby expressly incorporated by reference into the present application.

TECHNICAL FIELD

The present invention relates to a non-combustion type flavor inhaler having an atomizer that atomizes an aerosol source without burning.

BACKGROUND ART

Conventionally, a non-combustion type flavor inhaler for inhaling flavor without burning has been known. The non-combustion type flavor inhaler has a reservoir that stores an aerosol source, a capillary tube that sucks up the aerosol source from upstream toward downstream, and an atomizer that atomizes the aerosol source sucked up by the capillary tube. An upstream end of the capillary tube reaches the aerosol source stored in the reservoir, and the atomizer is disposed at a downstream end of the capillary tube (e.g., Patent Literatures 1 and 2).

CITATION LIST

Patent Literature

Patent Literature 1: WO 2013/083634 A
Patent Literature 2: JP 2005-537919 A

SUMMARY

A first feature is summarized as a non-combustion type flavor inhaler comprising: a reservoir storing an aerosol source; a transfer unit transferring the aerosol source from upstream of the liquid surface forming location to a liquid surface forming location at which a liquid surface of the aerosol source is formed, the transfer unit being configured to form the liquid surface; a suction port arranged downstream of the liquid surface forming location; a first atomizer atomizing the aerosol source located upstream of the liquid surface forming location; and a second atomizer atomizing a droplet generated from the liquid surface formed at the liquid surface forming location, the droplet being located downstream of the liquid surface forming location.

A second feature is summarized as the non-combustion type flavor inhaler according to the first feature, wherein the transfer unit is configured by a columnar member extending from upstream toward downstream, the columnar member holding the aerosol source such that the liquid surface is formed at the liquid surface forming location.

A third feature is summarized as the non-combustion type flavor inhaler according to the first feature or the second feature, wherein the first atomizer is arranged around the transfer unit at the liquid surface forming location, and the second atomizer is arranged downstream of the liquid surface faulting location.

A fourth feature is summarized as the non-combustion type flavor inhaler according to any one of the first feature to the third feature, wherein the transfer unit transfers the aerosol source by a capillary phenomenon.

A fifth feature is summarized as the non-combustion type flavor inhaler according to any one of the first feature to the fourth feature, wherein the transfer unit is formed by a tubular member transferring the aerosol source by a capillary phenomenon.

A sixth feature is summarized as the non-combustion type flavor inhaler according to the fifth feature, wherein the tubular member has a liquid surface defining part to define the liquid surface at the liquid surface forming location, the tubular member transferring the aerosol source to at least the liquid surface forming location, the tubular member including a portion extending downstream of the liquid surface forming location.

A seventh feature is summarized as the non-combustion type flavor inhaler according to the sixth feature, wherein the liquid surface defining part is configured by an opening disposed at the liquid surface forming location.

An eighth feature is summarized as the non-combustion type flavor inhaler according to the sixth feature, wherein an inner wall of the tubular member includes a step so that a hollow cross-sectional area on a downstream side of the liquid surface forming location is larger than a hollow cross-sectional area on the upstream side of the liquid surface forming location in an orthogonal cross section orthogonal to a direction from upstream toward downstream, and the liquid surface defining part is configured by the step.

A ninth feature is summarized as the non-combustion type flavor inhaler according to the eighth feature, wherein the tubular member comprises: a first pipe extending upstream from the liquid surface forming location; and a second pipe extending downstream at least from the liquid surface forming location, the second pipe is arranged outside the first pipe in the orthogonal cross section, and the step is formed by an inner wall of the first pipe, a downstream end of the first pipe, and an inner wall of the second pipe.

A tenth feature is summarized as the non-combustion type flavor inhaler according to the sixth feature, wherein a property of an inner wall of the tubular member is configured to change at the liquid surface forming location or on an upstream side of the liquid surface forming location.

An eleventh feature is summarized as the non-combustion type flavor inhaler according to any one of the sixth feature to the tenth feature, wherein the second atomizer is arranged around the tubular member on a downstream side of the liquid surface forming location.

A twelfth feature is summarized as the non-combustion type flavor inhaler according to any one of the first feature to the eleventh feature, wherein the first atomizer and the second atomizer are provided continuously over the liquid surface forming location.

DESCRIPTION OF EMBODIMENTS

Figure 1:
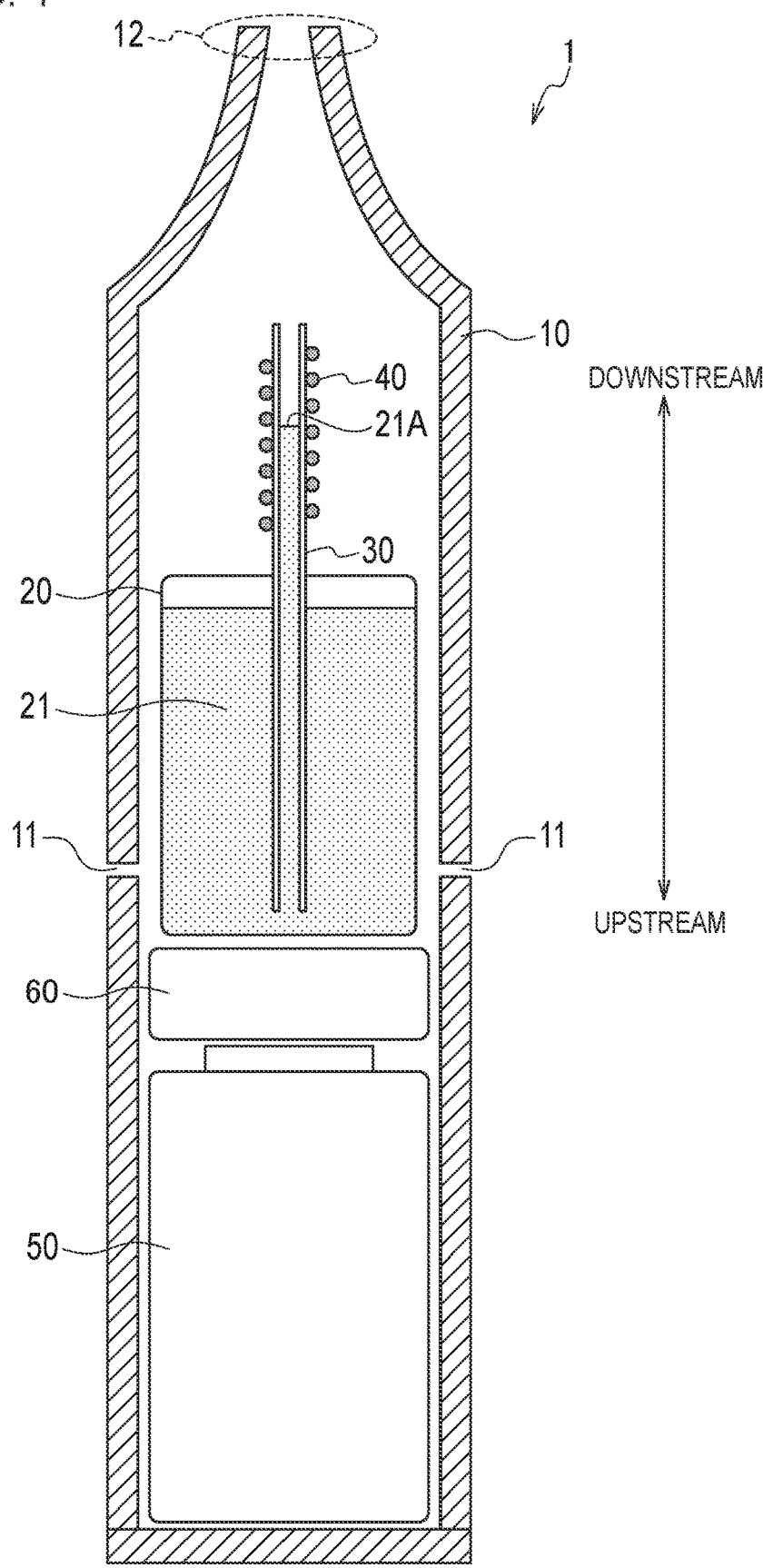
FIG. 1 is a view showing a flavor inhaler 1 according to an embodiment.

Hereinafter, the embodiments of the present invention will be described with reference to the drawings. In the following drawings, identical or similar components are denoted by identical or similar reference numerals.

Therefore, specific dimensions should be determined with reference to the description below. It is needless to mention that different relationships and ratio of dimensions may be included in different drawings.

SUMMARY OF EMBODIMENT

In the non-combustion type flavor inhaler described in the above background art, the aerosol source sucked up by the capillary tube reaches the downstream end of the capillary tube due to a capillary phenomenon. Therefore, a droplet with a large particle diameter may be scattered due to atomization of the aerosol source reaching the downstream end of the capillary tube.

A non-combustion type flavor inhaler according to an embodiment comprises: a reservoir storing an aerosol source; a transfer unit transferring the aerosol source from upstream of the liquid surface forming location to a liquid surface forming location at which a liquid surface of the aerosol source is formed, the transfer unit being configured to form the liquid surface; a suction port arranged downstream of the liquid surface forming location; a first atomizer atomizing the aerosol source located upstream of the liquid surface forming location; and a second atomizer atomizing a droplet generated from the liquid surface formed at the liquid surface forming location, the droplet being located downstream of the liquid surface forming location.

In the embodiment, the non-combustion type flavor inhaler includes the second atomizer that atomizes a droplet located downstream of the liquid surface forming location at which the liquid surface of the aerosol source is formed. This can suppress scattering of a droplet with a large particle diameter due to atomization of the aerosol source.

Embodiment (Non-Combustion Type Flavor Inhaler)

Hereinafter, a non-combustion type flavor inhaler according to an embodiment will be described. FIG. 1 is a view showing a non-combustion type flavor inhaler 1 according to the embodiment. The non-combustion type flavor inhaler 1 is a device for inhaling a flavoring component without burning. It should be noted that, in the following description, the non-combustion type flavor inhaler 1 is simply referred to as a flavor inhaler 1.

As shown in FIG. 1, the flavor inhaler 1 includes a housing 10, a storage container 20, a tubular member 30, an atomizer 40, a power source 50, and a control circuit 60.

The housing 10 accommodates each member forming the flavor inhaler 1. The housing 10 has an inlet 11 and a suction port 12. The inlet 11 is an opening to guide air into the housing 10. The suction port 12 is a portion to be held by a user's mouth, and is an opening to guide air into the user's mouth.

The storage container 20 stores the aerosol source 21. The aerosol source 21 is made of a raw material that generates aerosol by atomization. The aerosol source 21 is liquid made of an alcohol such as glycerin or propylene glycol, water, or their mixtures. The aerosol source 21 preferably contains a flavoring component. The flavoring component may be an extracted component extracted from various types of natural materials. The extracted component may be a tobacco extract component, or may be a tobacco smoke condensate component. Alternatively, the flavoring component may be a component such as menthol or caffeine.

The tubular member 30 is an example of a transfer unit that transfers the aerosol source 21 to the liquid surface forming location at which a liquid surface 21A of the aerosol source 21 is formed, from upstream of the liquid surface forming location, to form the liquid surface 21A. Further, the tubular member 30 is an example of a columnar member that extends from upstream toward downstream, and holds the aerosol source 21 such that the liquid surface 21A is formed at the liquid surface forming location.

In particular, it should be noted that the tubular member 30 transfers the aerosol source 21 by a capillary phenomenon, and holds the aerosol source 21 such that the liquid surface 21A of the aerosol source 21 is formed at the liquid surface forming location. Details of the tubular member 30 around the liquid surface forming location will be described later (see FIG. 2).

Here, "downstream" and "upstream" mean downstream and upstream in a transfer of fluid. Here, the fluid means the aerosol source 21, or the aerosol atomized by the atomizer 40. The transfer means transferring of the aerosol source 21 by a capillary phenomenon, or transferring of the aerosol source 21 or of the aerosol atomized by the atomizer 40, due to an inhalation action.

The atomizer 40 atomizes the aerosol source 21 held by the tubular member 30, near the liquid surface 21A of the aerosol source 21. In the embodiment, the atomizer 40 is formed by a coil-shaped heater wound around the tubular member 30. Details of the atomizer 40 around the liquid surface forming location will be described later (see FIG. 2).

The power source 50 is a battery that accumulates electric power to be consumed by the flavor inhaler 1. The power source 50 is a lithium-ion battery, for example.

The control circuit 60 controls the flavor inhaler 1. The control circuit 60 is configured by, for example, a CPU and a memory. Specifically, the control circuit 60 is connected to an inhalation operation interface (such as an inhalation button) that can be operated by a user. In a time duration in which the inhalation operation interface is being operated by the user, the control circuit 60 supplies a power output to the atomizer 40. On the other hand, the control circuit 60 stops the supply of the power output to the atomizer 40 in a time duration in which the inhalation operation interface is not being operated by the user. Alternatively, the control circuit 60 is connected to a suction sensor that detects an inhalation action, and supplies the power output to the atomizer 40 in a time duration in which an inhalation action is being performed. On the other hand, the control circuit 60 stops the supply of the power output to the atomizer 40 in a time duration in which an inhalation action is not being performed.

(Configuration Around Liquid Surface Forming Location)

Hereinafter, a configuration around the liquid surface forming location according to the embodiment will be described. FIG. 2 is a view showing a configuration around the liquid surface forming location according to the embodiment.

As shown in FIG. 2, the tubular member 30 has an opening 31 disposed at the liquid surface forming location, and has a portion extending downstream from the liquid surface forming location. The opening 31 constitutes a liquid surface defining part that defines the liquid surface 21A.

In the embodiment, in the tubular member 30, an upstream portion from the opening 31 has a function of transferring the aerosol source 21 to the liquid surface forming location by a capillary phenomenon. In the tubular member 30, a downstream portion from the opening 31 has a function of guiding a droplet scattered due to atomization, to a position where the droplet can be heated by a second atomizer 42.

In the embodiment, a plurality of openings 31 may be intermittently provided along a circumferential direction of the tubular member 30. Alternatively, a single opening 31 may be continuously provided over the entire circumference of the tubular member 30. That is, the tubular member 30 may be separated into two tubular members near the liquid surface forming location.

The atomizer 40 includes a first atomizer 41 that atomizes the aerosol source 21 located upstream of the liquid surface forming location, and the second atomizer 42 that atomizes a droplet generated from the liquid surface formed at the liquid surface forming location and located downstream of the liquid surface forming location. In the embodiment, the first atomizer 41 is arranged around the tubular member 30 at the liquid surface forming location, and the second atomizer 42 is arranged around the tubular member 30, on the downstream side of the liquid surface forming location. The first atomizer 41 and the second atomizer 42 are preferably provided continuously over the liquid surface forming location.

(Function and Effect)

In the embodiment, the flavor inhaler 1 includes the second atomizer 42 that atomizes a droplet located downstream of the liquid surface forming location at which the liquid surface 21A of the aerosol source 21 is formed. This can suppress scattering of a droplet with a large particle diameter due to atomization of the aerosol source 21.

In the embodiment, the tubular member 30 extends downstream of the liquid surface forming location, and has the opening 31 disposed at the liquid surface forming location. The opening 31 constitutes a liquid surface defining part that defines the liquid surface 21A. As a result, since the liquid surface 21A can be formed in a middle of the tubular member 30 instead of the downstream end of the tubular member 30, the second atomizer 42 can be easily arranged downstream of the liquid surface forming location. It is easy to guide the a droplet scattered due to the atomization of the aerosol source 21, to a position where the droplet can be heated by the second atomizer 42.

In the embodiment, the second atomizer 42 is arranged around the tubular member 30, on the downstream side of the liquid surface forming location. Therefore, the second atomizer 42 can be easily disposed at a position where it is easy to atomize a droplet located downstream of the liquid surface forming location.

In the embodiment, the first atomizer 41 and the second atomizer 42 are continuously provided over the liquid surface forming location. Therefore, it is easy to arrange and configure the atomizer 40 configured by the first atomizer 41 and the second atomizer 42.

Modified Example 1

Hereinafter, Modified Example 1 of the embodiment will be described. In the following, differences from the embodiment will be mainly described.

Specifically, in the embodiment, the liquid surface defining part that defines the liquid surface 21A is constituted by the opening 31 disposed at the liquid surface forming location. On the other hand, in Modified Example 1, a liquid surface defining part that defines a liquid surface 21A is constituted by a step provided on an inner wall of a tubular member 30.

(Configuration Around Liquid Surface Forming Location)

Hereinafter, a configuration around the liquid surface forming location according to Modified Example 1 will be described. FIG. 3 is a view showing a configuration around the liquid surface forming location according to Modified Example 1.

As shown in FIG. 3, the tubular member 30 includes a first pipe 32 extending upstream from the liquid surface forming location, and a second pipe 33 extending downstream at least from the liquid surface forming location. The second pipe 33 is arranged outside the first pipe 32 in an orthogonal cross section orthogonal to a direction from upstream toward downstream.

In Modified Example 1, the second pipe 33 may extend from upstream toward downstream of the liquid surface forming location. In other words, the first pipe 32 and the second pipe 33 may overlap each other at the liquid surface forming location.

In such a case, a liquid surface defining part that defines the liquid surface 21A is constituted by a step 34 formed by an inner wall 32A of the first pipe 32, a downstream end 32B of the first pipe 32, and an inner wall 33A of the second pipe 33. In other words, in the orthogonal cross section orthogonal to the direction from upstream toward downstream, the inner wall of the tubular member 30 has the step 34 having a larger hollow cross-sectional area on the downstream side of the liquid surface forming location than a hollow cross-sectional area on the upstream side of the liquid surface forming location. That is, the liquid surface forming location is provided at a boundary of different hollow cross-sectional areas.

In Modified Example 1, the first pipe 32 has a function of transferring the aerosol source 21 to the liquid surface forming location by a capillary phenomenon. The second pipe 33 has a function of guiding a droplet scattered due to atomization, to a position where the droplet can be heated by the second atomizer 42.

In Modified Example 1, a first atomizer 41 is arranged around the first pipe 32 and the second pipe 33 at the liquid surface forming location, and a second atomizer 42 is arranged around the second pipe 33, on the downstream side of the liquid surface forming location. The first atomizer 41 and the second atomizer 42 are preferably provided continuously over the liquid surface forming location.

(Function and Effect)

In Modified Example 1, the step 34 is provided as the liquid surface defining part instead of the opening 31, but similar effects to the embodiment can be obtained. Further, since the opening 31 is unnecessary, no droplet leaks from the opening 31.

Modified Example 2

Hereinafter, Modified Example 2 of the embodiment will be described. In the following, differences from the embodiment will be mainly described.

Specifically, in the embodiment, the liquid surface defining part that defines the liquid surface 21A is constituted by the opening 31 disposed at the liquid surface forming location. On the other hand, in Modified Example 2, a liquid surface defining part that defines a liquid surface 21A is constituted by a step provided on an inner wall of a tubular member 30.

(Configuration Around Liquid Surface Forming Location)

Figure 4:
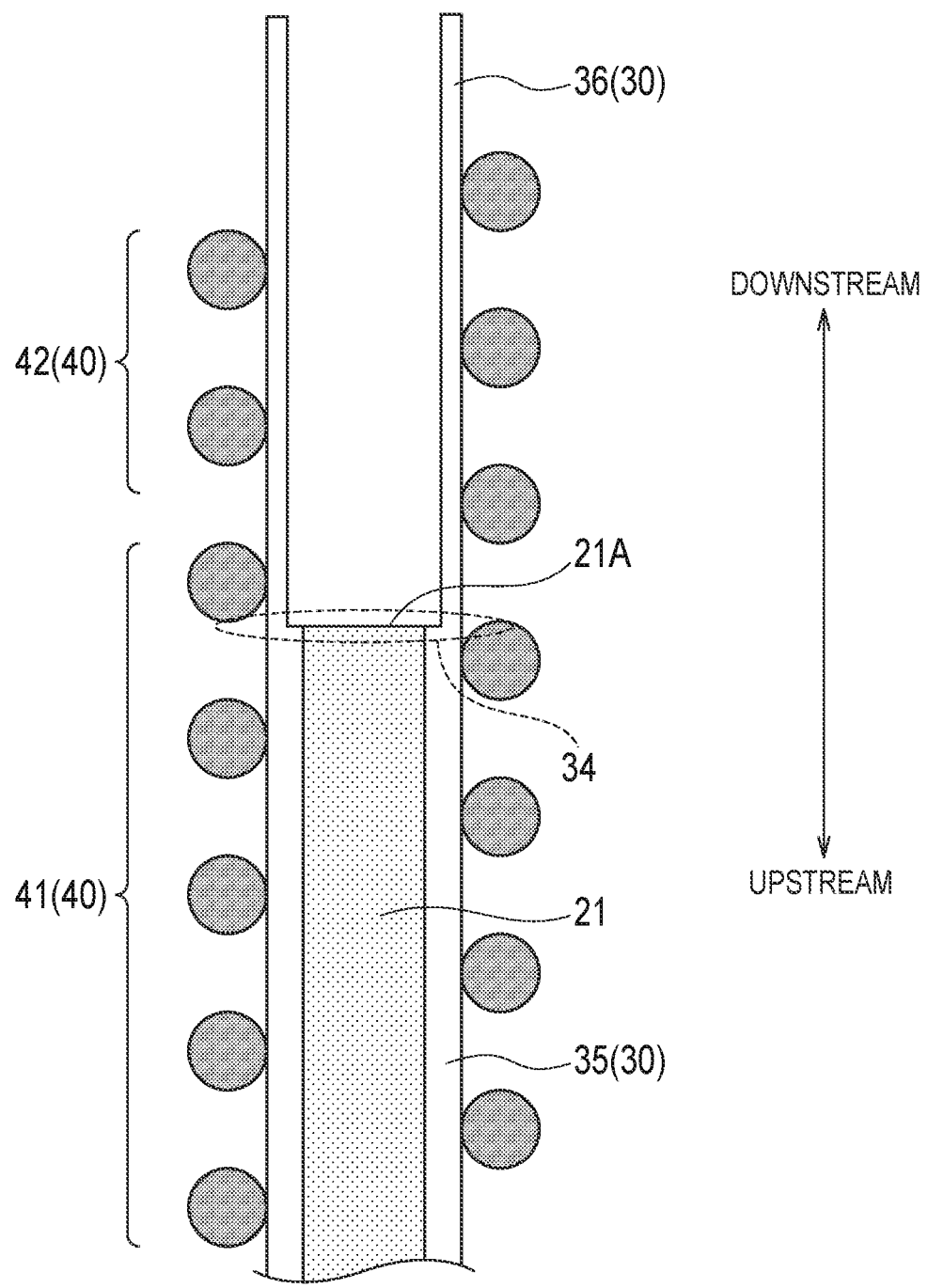
FIG. 4 is a view showing a configuration around a liquid surface forming location according to Modified Example 2.

Hereinafter, a configuration around the liquid surface forming location according to Modified Example 2 will be described. FIG. 4 is a view showing a configuration around the liquid surface forming location according to Modified Example 2.

As shown in FIG. 4, the tubular member 30 includes a first portion 35 extending upstream from the liquid surface forming location, and a second portion 36 extending downstream from the liquid surface forming location. In an orthogonal cross section orthogonal to a direction from upstream toward downstream, a hollow cross-sectional area of the second portion 36 is larger than a hollow cross-sectional area of the first portion 35.

In such a case, the liquid surface defining part that defines the liquid surface 21A is constituted by a step 34 formed by a boundary between the first portion 35 and the second portion 36. In other words, in the orthogonal cross section orthogonal to the direction from upstream toward downstream, the inner wall of the tubular member 30 has the step 34 having a larger hollow cross-sectional area on the downstream side of the liquid surface forming location than a hollow cross-sectional area on the upstream side of the liquid surface forming location.

In Modified Example 2, the first portion 35 has a function of transferring the aerosol source 21 to the liquid surface forming location by a capillary phenomenon. The second portion 36 has a function of guiding a droplet scattered due to atomization, to a position where the droplet can be heated by a second atomizer 42.

In Modified Example 2, the first atomizer 41 is arranged around the first portion 35 and the second portion 36 at the liquid surface forming location, and the second atomizer 42 is arranged around the second portion 36, on the downstream side of the liquid surface forming location. The first atomizer 41 and the second atomizer 42 are preferably provided continuously over the liquid surface forming location.

(Function and Effect)

In Modified Example 2, the step 34 is provided as the liquid surface defining part instead of the opening 31, but similar effects to the embodiment can be obtained. Further, since the opening 31 is unnecessary, no droplet leaks from the opening 31.

Modified Example 3

Hereinafter, Modified Example 3 of the embodiment will be described. In the following, differences from the embodiment will be mainly described.

Specifically, in the embodiment, the liquid surface defining part that defines the liquid surface 21A is constituted by the opening 31 disposed at the liquid surface forming location. On the other hand, in Modified Example 3, a liquid surface defining part that defines a liquid surface 21A is constituted by a step provided on an inner wall of a tubular member 30.

(Configuration Around Liquid Surface Forming Location)

Figure 5:
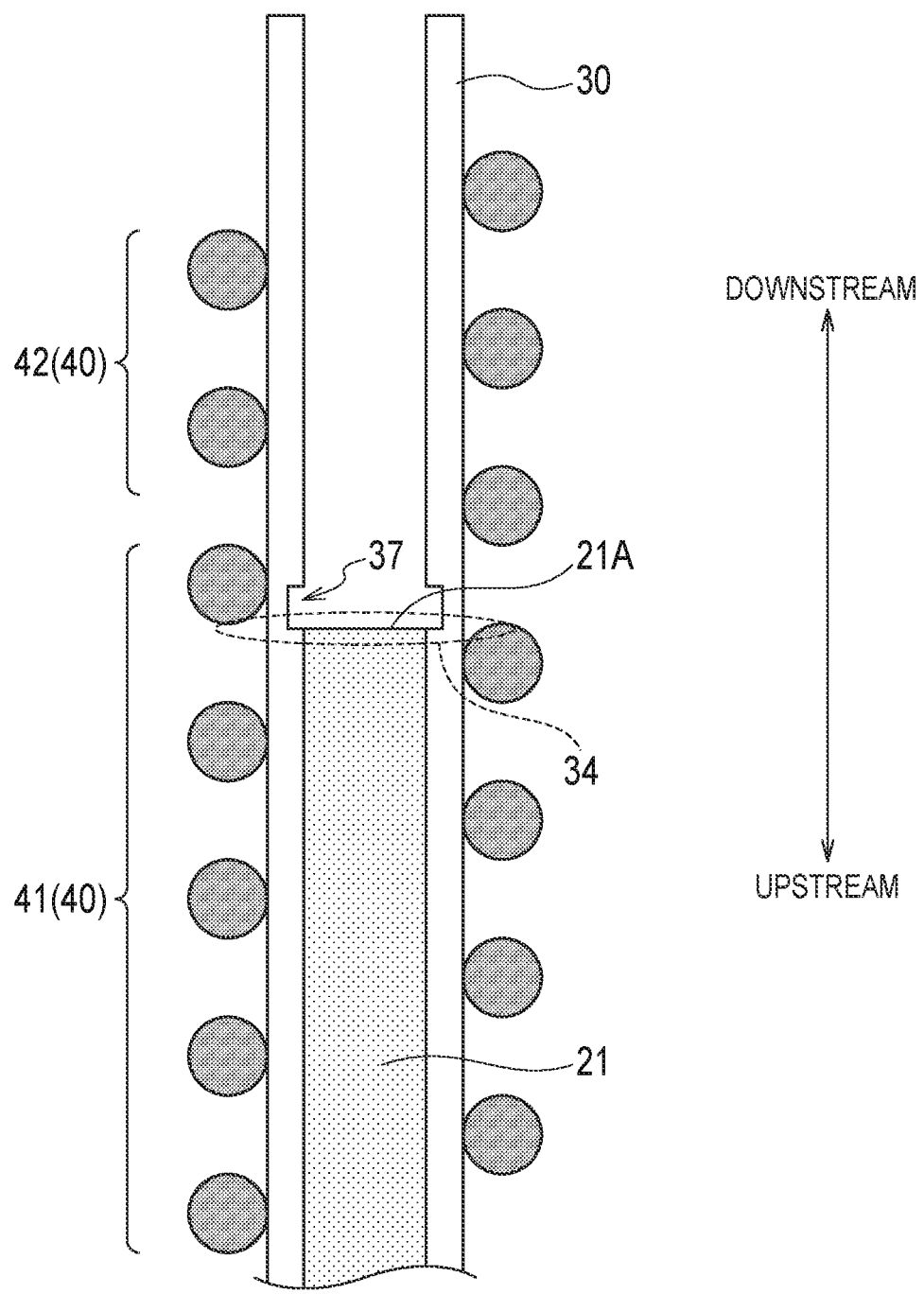
FIG. 5 is a view showing a configuration around a liquid surface forming location according to Modified Example 3.

Hereinafter, a configuration around the liquid surface forming location according to Modified Example 3 will be described. FIG. 5 is a view showing a configuration around the liquid surface forming location according to Modified Example 3.

As shown in FIG. 5, the inner wall of the tubular member 30 has a recess 37 provided at the liquid surface forming location. The liquid surface defining part that defines the liquid surface 21A is constituted by a step 34 that is formed by an upstream portion of the recess 37. In other words, in an orthogonal cross section orthogonal to a direction from upstream toward downstream, the inner wall of the tubular member 30 has the step 34 having a larger hollow cross-sectional area on the downstream side of the liquid surface forming location than a hollow cross-sectional area on the upstream side of the liquid surface forming location.

In Modified Example 3, a plurality of recesses 37 may be intermittently provided along a circumferential direction of the tubular member 30. Alternatively, a single recess 37 may be continuously provided over the entire circumference of the tubular member 30.

In Modified Example 3, in the tubular member 30, the upstream portion from the recess 37 has a function of transferring the aerosol source 21 to the liquid surface forming location by a capillary phenomenon. In the tubular member 30, a downstream portion from the recess 37 has a function of guiding the a droplet scattered due to atomization, to a position where the droplet can be heated by the second atomizer 42.

In Modified Example 3, the first atomizer 41 is arranged around the tubular member 30 at the liquid surface forming location, and the second atomizer 42 is arranged around the tubular member 30, on the downstream side of the liquid surface forming location. The first atomizer 41 and the second atomizer 42 are preferably provided continuously over the liquid surface forming location.

(Function and Effect)

In Modified Example 3, the step 34 is provided as the liquid surface defining part instead of the opening 31, but similar effects to the embodiment can be obtained. Further, since the opening 31 is unnecessary, no droplet leaks from the opening 31.

Modified Example 4

Hereinafter, Modified Example 4 of the embodiment will be described. In the following, differences from the embodiment will be mainly described.

Specifically, in the embodiment, the liquid surface defining part that defines the liquid surface 21A is constituted by the opening 31 disposed at the liquid surface forming location. On the other hand, in Modified Example 4, a property of an inner wall of a tubular member 30 is changed at the liquid surface forming location or on an upstream side of the liquid surface forming location.

(Configuration Around Liquid Surface Forming Location)

Figure 6:
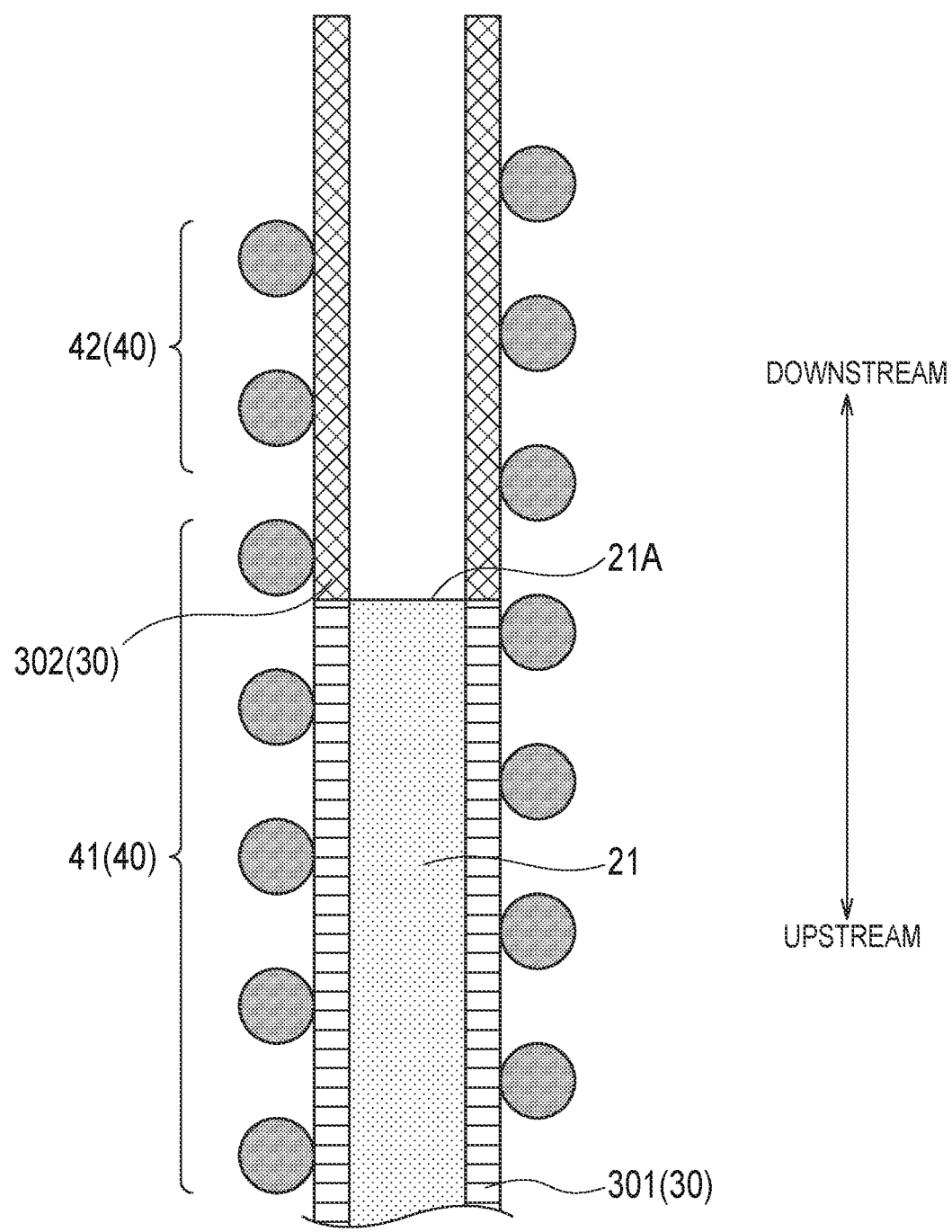
FIG. 6 is a view showing a configuration around a liquid surface forming location according to Modified Example 4.

Hereinafter, a configuration around the liquid surface forming location according to Modified Example 4 will be described. FIG. 6 is a view showing a configuration around a liquid surface forming location according to Modified Example 4.

As shown in FIG. 6, the tubular member 30 includes a first portion 301 extending upstream from the liquid surface forming location, a second portion 302 continuous with the first portion 301 and extending downstream from the liquid surface forming location.

Here, the property of the inner wall of the tubular member 30 is changed at the liquid surface forming location. That is, a property of an inner wall of the second portion 302 is different from a property of an inner wall of the first portion 301. In FIG. 6, the property of the inner wall of the tubular member 30 is changed at the liquid surface forming location, but the property may be changed on the upstream side of the liquid surface forming location. The property of the inner wall is a property that affects the capillary phenomenon, for example, wettability of the inner wall against the aerosol source 21. In particular, wettability of the inner wall of the second portion 302 against the aerosol source 21 is poor as compared to wettability of the inner wall of the first portion 301 against the aerosol source 21. Accordingly, the inner wall of the second portion 302 constitutes a liquid surface defining part that defines the liquid surface 21A.

Here, wettability of the inner wall of the tubular member 30 against the aerosol source 21 depends on a material and a surface roughness of the inner wall of the first portion 301 and the inner wall of the second portion 302. By changing the material and the surface roughness of the inner wall of the first portion 301 and the inner wall of the second portion 302, the wettability of the inner wall of the tubular member 30 against the aerosol source 21 can be changed.

In Modified Example 3, the first portion 301 has a function of transferring the aerosol source 21 to the liquid surface forming location by a capillary phenomenon. The second portion 302 has a function of guiding a droplet scattered due to atomization, to a position where the droplet can be heated by the second atomizer 42.

In Modified Example 4, the first atomizer 41 is arranged around the first portion 301 and the second portion 302 at the liquid surface forming location, and the second atomizer 42 is arranged around the second portion 302, on the downstream side of the liquid surface forming location. The first atomizer 41 and the second atomizer 42 are preferably provided continuously over the liquid surface forming location.

(Function and Effect)

In Modified Example 4, instead of the opening 31, the liquid surface defining part is constituted by a change in the property of the inner wall of the tubular member 30, but similar effects to the embodiment can be obtained. Further, since the opening 31 is unnecessary, no droplet leaks from the opening 31.

Modified Example 5

Hereinafter, Modified Example 5 of the embodiment will be described. In the following, differences from the embodiment will be mainly described.

Specifically, in the embodiment, the tubular member 30 has been exemplified as a transfer unit that forms the liquid surface 21A of the aerosol source 21 at the liquid surface forming location. On the other hand, in Modified Example 5, the transfer unit is a fibrous member formed by twisting glass fibers or the like.

(Non-Combustion Type Flavor Inhaler)

Figure 7:
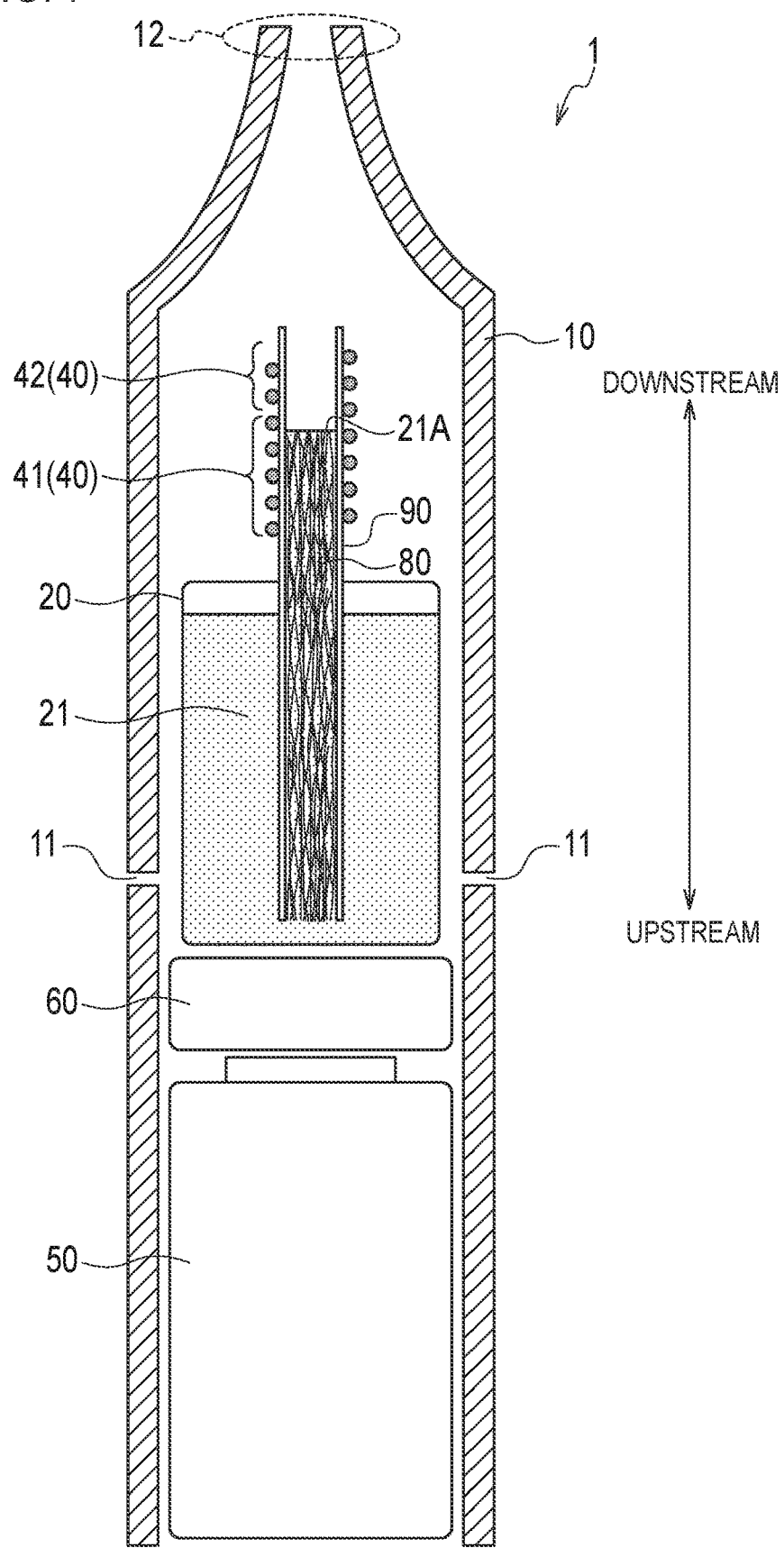
FIG. 7 is a view showing a flavor inhaler 1 according to Modified Example 5.

Hereinafter, a non-combustion type flavor inhaler according to Modified Example 5 will be described. FIG. 7 is a view showing a flavor inhaler 1 according to Modified Example 5. However, in FIG. 7, only a part of the flavor inhaler 1 is shown, and a storage container 20, a power source 50, a control circuit 60, and the like are omitted.

As shown in FIG. 7, the flavor inhaler 1 has a fibrous member 80 and a holding member 90 instead of the tubular member 30.

The fibrous member 80 is an example of a transfer unit that transfers an aerosol source 21 to a liquid surface forming location at which a liquid surface 21A of the aerosol source 21 is formed, from upstream of the liquid surface forming location, to form the liquid surface 21A.

Specifically, the fibrous member 80 is formed by twisting glass fibers or the like. A capillary phenomenon occurs due to a space between the glass fibers. Therefore, it should be noted that the fibrous member 80 is an example of a columnar member that transfers the aerosol source 21 by a capillary phenomenon, and holds the aerosol source 21 such that the liquid surface 21A of the aerosol source 21 is formed at the liquid surface forming location. In Modified Example 5, a liquid surface defining part that defines the liquid surface 21A is constituted by the downstream end of the fibrous member 80.

The holding member 90 is a member to maintain a shape of the fibrous member 80. Specifically, the holding member 90 has a tubular shape, and the fibrous member 80 is disposed inside the holding member 90. The holding member 90 preferably extends downstream of the liquid surface forming location (the downstream end of the fibrous member 80). It should to be noted that a cavity of the holding member 90 has a size that does not cause a capillary phenomenon.

In Modified Example 5, the first atomizer 41 is arranged around the holding member 90 at the liquid surface forming location, and the second atomizer 42 is arranged around the holding member 90, on the downstream side of the liquid surface forming location. The first atomizer 41 and the second atomizer 42 are preferably provided continuously over the liquid surface forming location.

When the fibrous member 80 has hardness enough to maintain the shape of the fibrous member 80, the holding member 90 may be omitted. In such a case, the first atomizer 41 is arranged around the fibrous member 80 at the liquid surface forming location. The second atomizer 42 only needs to be arranged downstream of the liquid surface forming location. For example, the second atomizer 42 may be arranged near the suction port 12 on an inner wall of a housing 10.

(Function and Effect)

In Modified Example 5, the fibrous member 80 is used instead of the tubular member 30, but effects of the embodiment can be obtained. In addition, since a hollow cross-sectional area (cross-sectional area of the fibrous member 80) of the holding member 90 is larger than a hollow cross-sectional area of the tubular member 30, the fibrous member 80 can hold a larger amount of the aerosol source 21 than that in the embodiment.

Other Embodiments

Although the present invention has been described with the above-described embodiments, the descriptions and drawings forming a part of the disclosure should not be construed as limiting the present invention. From this disclosure, various alternative embodiments, examples, and operation techniques will be apparent to those skilled in the art.

In the embodiment, the first atomizer 41 and the second atomizer 42 are continuously provided over the liquid surface forming location. However, the embodiment is not limited to this. The first atomizer 41 and the second atomizer 42 may be separate members discontinuous with each other.

In the embodiment, the coil-shaped heater wound around the tubular member 30 or the like has been exemplified as the first atomizer and the second atomizer. However, the embodiment is not limited to this. The first atomizer only needs to have a function of atomizing the aerosol source located upstream of the liquid surface forming location. The second atomizer only needs to atomize a droplet located downstream of the liquid surface forming location. For example, the first atomizer and the second atomizer may be a heater type atomizer, or may be an ultrasonic type atomizer. The type of the first atomizer may be different from the type of the second atomizer.

Although not specifically mentioned in the embodiment, the tubular member 30 has a capillary tube that transfers the aerosol source 21 to the liquid surface forming location by a capillary phenomenon, and a guide tube that guides a droplet scattered due to atomization, to a position where the droplet can be heated by the second atomizer 42. The capillary tube and the guide tube may be separate members, or may be a same member. The capillary tube and the guide tube may or may not be in contact with each other.

Figure 2:
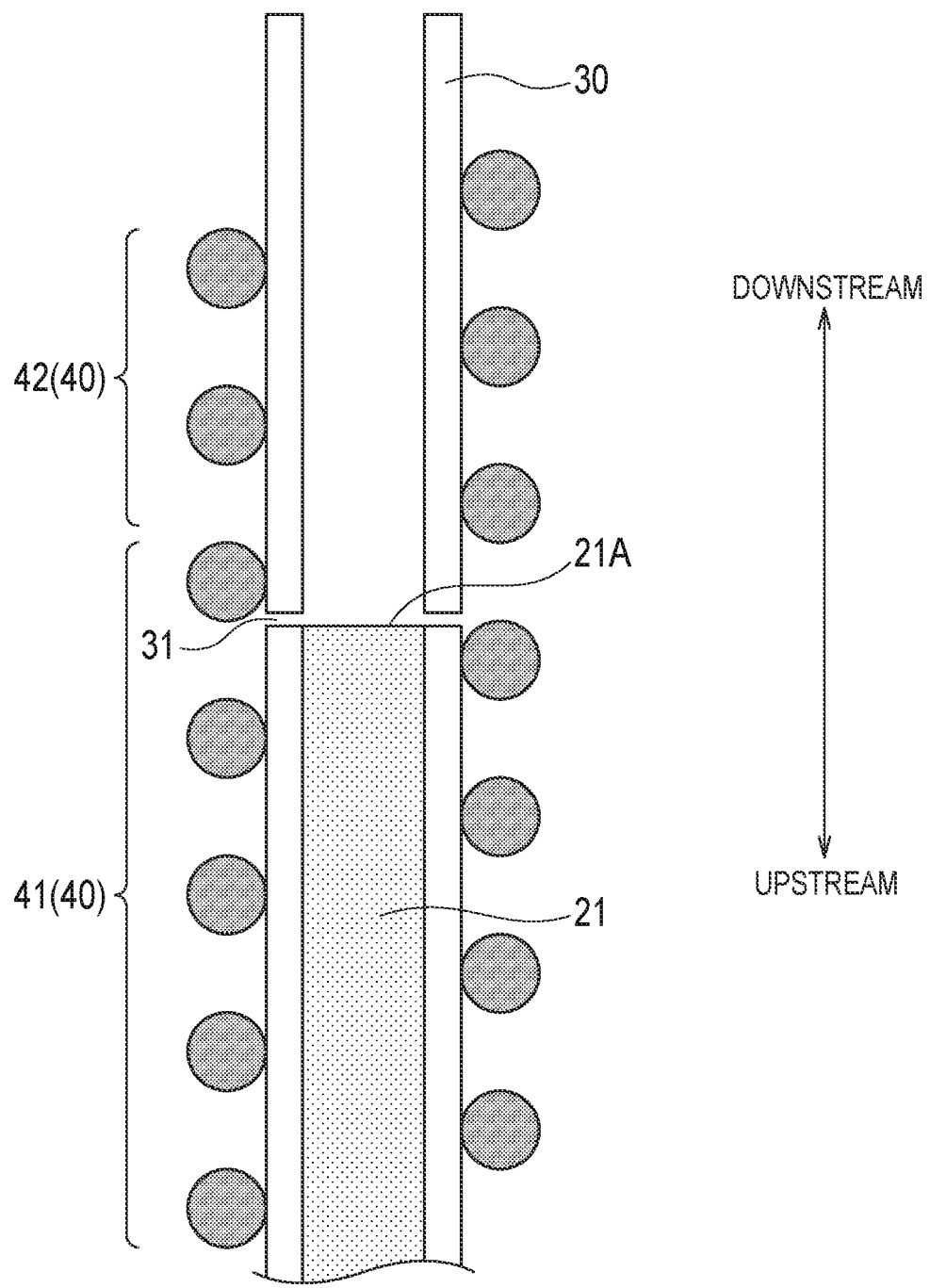
FIG. 2 is a view showing a configuration around a liquid surface forming location according to the embodiment.
Figure 3:
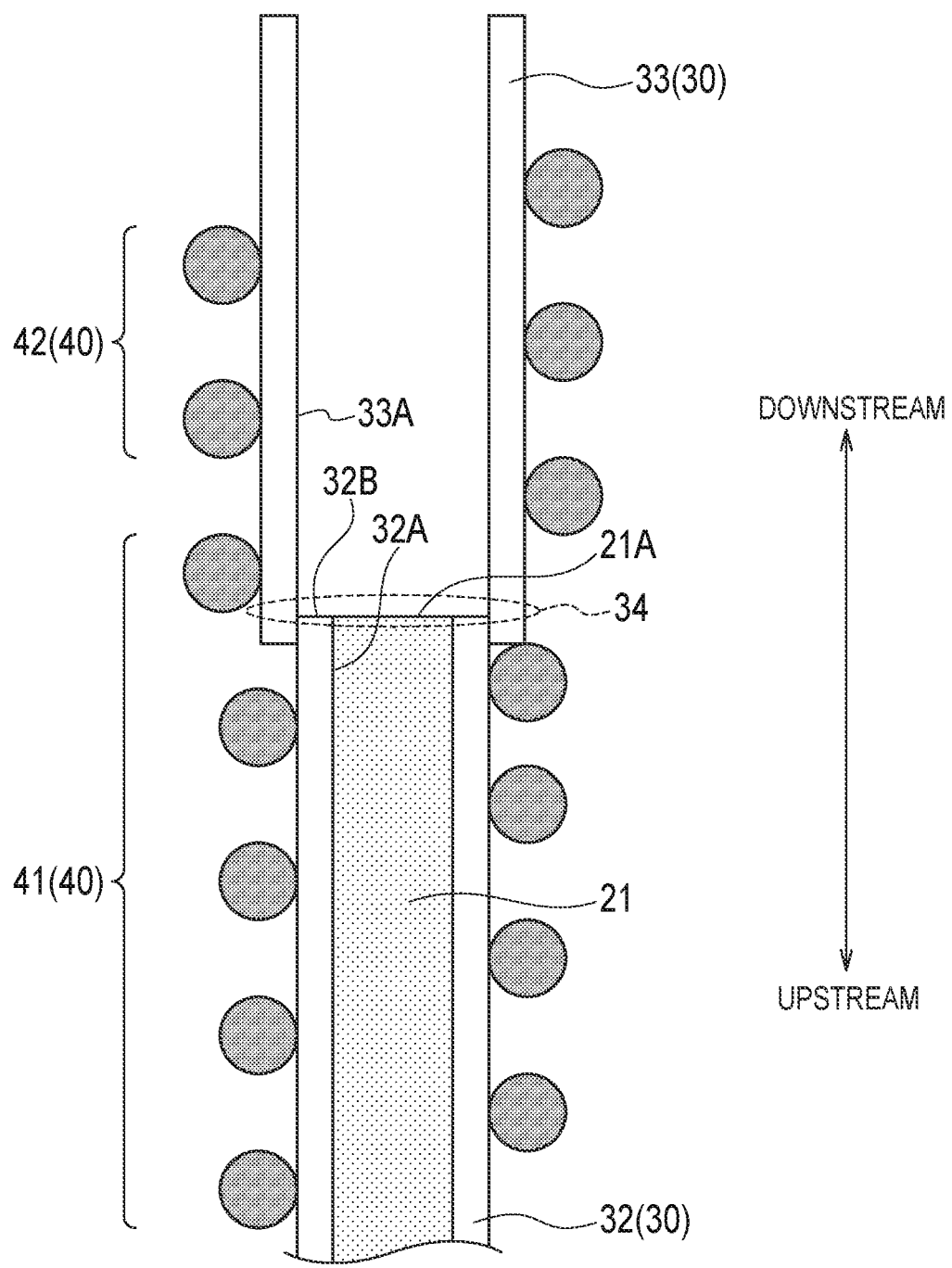
FIG. 3 is a view showing a configuration around a liquid surface forming location according to Modified Example 1.

The guide tube may have a capillary function. It should be noted that, even in such a case, the liquid surface 21A is formed at the liquid surface forming location due to the presence of the liquid surface defining part. Further, as in the embodiment (FIG. 2), the tubular member 30 may be a member provided with the opening 31 at the liquid surface forming location of one capillary tube.

INDUSTRIAL APPLICABILITY

According to the embodiment, it is possible to provide the non-combustion type flavor inhaler capable of suppressing scattering of a droplet having a large particle diameter due to atomization of the aerosol source.

The invention claimed is:

1. A non-combustion type flavor inhaler comprising:
a reservoir storing an aerosol source;
a transfer unit transferring the aerosol source from upstream of a liquid surface forming location at which a liquid surface of the aerosol source is formed to the liquid surface forming location, the transfer unit being configured to form the liquid surface;
a suction port arranged downstream of the liquid surface forming location;
a first atomizer atomizing the aerosol source located upstream of the liquid surface forming location; and
a second atomizer atomizing a droplet generated from the liquid surface formed at the liquid surface forming location, the droplet being located downstream of the liquid surface forming location,
wherein the transfer unit is formed by a tubular member transferring the aerosol source by a capillary phenomenon,
wherein the tubular member has a liquid surface defining part to define the liquid surface at the liquid surface forming location, the tubular member transferring the aerosol source to at least the liquid surface forming location, the tubular member including a portion extending downstream of the liquid surface forming location, and
wherein the liquid surface defining part is configured by an opening communicating an inside surface of the tubular member with an outside surface of the tubular member.

2. The non-combustion type flavor inhaler according to claim 1, wherein the transfer unit is configured by a columnar member extending from upstream toward downstream, the columnar member holding the aerosol source such that the liquid surface is formed at the liquid surface forming location.

3. The non-combustion type flavor inhaler according to claim 1, wherein the first atomizer is arranged around the transfer unit at the liquid surface forming location, and
the second atomizer is arranged downstream of the liquid surface forming location.

4. The non-combustion type flavor inhaler according to claim 1, wherein the second atomizer is arranged around the tubular member on a downstream side of the liquid surface forming location.

5. The non-combustion type flavor inhaler according to claim 1, wherein the first atomizer and the second atomizer are provided continuously over the liquid surface forming location.

6. The non-combustion type flavor inhaler according to claim 1, wherein the opening is formed radially through a sidewall of the tubular member at the liquid surface forming location.

7. A non-combustion type flavor inhaler comprising:
a reservoir storing an aerosol source;
a transfer unit transferring the aerosol source from upstream of a liquid surface forming location at which a liquid surface of the aerosol source is formed to the liquid surface forming location, the transfer unit being configured to form the liquid surface;
a suction port arranged downstream of the liquid surface forming location;
a first atomizer atomizing the aerosol source located upstream of the liquid surface forming location; and
a second atomizer atomizing a droplet generated from the liquid surface formed at the liquid surface forming location, the droplet being located downstream of the liquid surface forming location,
wherein the transfer unit is formed by a tubular member transferring the aerosol source by a capillary phenomenon,
wherein the tubular member has a liquid surface defining part to define the liquid surface at the liquid surface forming location, the tubular member transferring the aerosol source to at least the liquid surface forming location, the tubular member including a portion extending downstream of the liquid surface forming location, and
wherein the liquid surface defining part comprises
wherein wettability of an inner wall of the tubular member is configured to change at the liquid surface forming location or on an upstream side of the liquid surface forming location.

* * * * *